United States Patent [19]

Biden et al.

[11] Patent Number: 5,595,902
[45] Date of Patent: Jan. 21, 1997

[54] DNA ENCODING HUMAN PROTEIN KINASE C (IOTA)

[75] Inventors: Trevor J. Biden, Neutral Bay; Lisa Selbie, McMahons Point, both of Australia

[73] Assignee: Garvan Institute of Medical Research, Darlinghurst, Australia

[21] Appl. No.: 313,274

[22] PCT Filed: Feb. 4, 1994

[86] PCT No.: PCT/AU94/00052

§ 371 Date: Dec. 2, 1994

§ 102(e) Date: Dec. 2, 1994

[87] PCT Pub. No.: WO94/18328

PCT Pub. Date: Aug. 18, 1994

[30] Foreign Application Priority Data

| Feb. 6, 1993 | [GB] | United Kingdom | 9302342 |
| Feb. 6, 1993 | [GB] | United Kingdom | 9302343 |
| Feb. 6, 1993 | [GB] | United Kingdom | 9302360 |
| Feb. 6, 1993 | [GB] | United Kingdom | 9302361 |
| Sep. 16, 1993 | [GB] | United Kingdom | 9319147 |
| Sep. 16, 1993 | [GB] | United Kingdom | 9319148 |
| Sep. 16, 1993 | [GB] | United Kingdom | 9319149 |
| Sep. 16, 1993 | [GB] | United Kingdom | 9319150 |

[51] Int. Cl.$^6$ ............... C12N 5/10; C12N 9/12; C12N 15/54
[52] U.S. Cl. ............ 435/240.1; 435/194; 435/320.1; 435/252.3; 435/240.2; 435/240.4; 536/23.2
[58] Field of Search ............... 435/194, 320.1, 435/252.3, 240.1, 240.2, 240.4; 536/23.2

[56] References Cited

PUBLICATIONS

Liyanage et al., Biochem. J., vol. 283: 781–787 1992.
Selbie et al., J. Biol. Chem., vol. 268, No. 32, pp. 24296–24302, iss. Nov. 15, 1993.
Goodnight et al., Gene, vol. 122, pp. 305–311 1992.

*Primary Examiner*—Keith D. Hendricks
*Attorney, Agent, or Firm*—Rothwell, Figg, Ernst & Kurz

[57] ABSTRACT

The present invention relates to protein kinase C (iota). The present invention provides this protein in a substantially pure form and also provides nucleotide sequences encoding the protein. The invention further relates to methods of screening for compounds having human protein kinase C (iota) agonist or antagonist activity.

6 Claims, No Drawings

DNA ENCODING HUMAN PROTEIN KINASE C (IOTA)

The present invention relates to a novel protein, compounds useful for the regulation of the activity of such protein, screening methods for identifying such compounds, the use of such protein and compounds in medicine, end to DNA sequences encoding the protein.

Protein kinase C is the name given to a family of enzymes that contain a regulatory unit with a binding site for phospholipid or diacylglycerol and a catalytic unit containing an ATP binding site. Some members of the family also contain a $Ca^{2+}$ binding site. The enzymes are important regulatory proteins in the signal transduction process by which the cells respond to signals received at cell surface receptors. Typically, protein kinase C is activated by diacylglycerol released from the action of phospholipase C on phosphatidylinositol ($PIP_2$). Binding of diacylglycerol to protein kinase C in the presence of ATP results in activation of the protein kinase C and it can then phosphorylate other enzymes involved in metabolic processes thereby regulating the metabolic processes. The specificity of the protein substrate for phosphorylation by protean kinase C is dependent on the particular isoform.

Several isoforms of protein kinase C have already been identified and these have been given the subscripts alpha, beta, beta II, gamma, delta, epsilon and zeta. We have now identified a further, novel isoform of protein kinase C which differs from the zeta isoform chiefly in the amino terminal region—a region believed to be important in the determination of substrate specificity.

The novel protein kinase C of the present invention is named protean kinase C (iota). The deduced amino acid sequence of the novel protein suggests that it is atypical protein kinase C which is most probably not activated by diacylglycerol derived from $PIP_2$. The mRNA encoding for the novel protein has been shown to be present in hamster insulinoma cells (HIT cells) and rat insulinoma cells (RIN) and also in isolated pancreatic islets from rats. Its presence in these cell lines and pancreatic islets suggests that it is involved in the regulation of the activity of hormones that originate in the pancreatic islets and are involved in the control of glycaemia, for example hormones such as insulin, glucagon and amylin. This is especially true of the capacity of glucose and other nutrients to stimulate the release of these hormones, since the nutrients generate diacylglycerol and other lipids, which might activate the novel protein, through pathways other than $PIP_2$ breakdown. The regulation of the activity of protein kinase C (iota) is therefore considered to have important potential in the treatment of diabetes.

There is experimental evidence that the atypical protein kinase C zeta isoform is activated by certain growth factors. Our laboratory has now shown that protein kinase C iota binds to another protein, ras-GAP, which is known to act in the chain of events initiated by growth factors that act on receptor tyrosine kinase. The regulation of the activity of protein kinase C iota is therefore considered to have important potential in the treatment of cancer.

Accordingly, in a first aspect the present invention consists in a DNA molecule which encodes human protein kinase C (iota), the DNA molecule having a sequence substantially as shown in Table 1 or a complementary sequence or a sequence which hybridizes thereto under stringent conditions.

Also provided are a vector comprising such a sequence, a host cell transformed with such a vector and recombinant proteins encoded for such a sequence.

In a second aspect the present invention consists in a method of producing protein kinase C (iota) comprising culturing the cell including the DNA molecule of the first aspect of the present invention under conditions which allow expression of the DNA molecule encoding human protein kinase C (iota) and recovering the expressed protein kinase C (iota).

In a third aspect the present invention consists in human protein kinase C (iota) in a substantially pure form.

In a fourth aspect the present invention consists in a method of treating diabetes in a subject suffering from diabetes comprising administering to the subject a composition comprising a protein kinase C (iota) agonist and a carrier.

In a fifth aspect the present invention consists in a method of treating cancer in a subject suffering from cancer comprising administering to the subject a composition comprising a protein kinase C (iota) antagonist and a carrier.

As there is high expression of protein kinase in the lung it is believed that this method may be of particular use in the treatment of lung cancer.

In a sixth aspect the present invention consists in a method of treating asthma in a subject suffering from asthma comprising administering to the subject a composition comprising a protein kinase C (iota) antagonist and a carrier.

In a seventh aspect the present invention consists in a method of screening a compound for ability to regulate expression of human protein kinase C (iota) in a cell comprising exposing the cell transformed with the DNA molecule of the first aspect of the present invention to the compound and assessing the level of expression of the DNA sequence encoding human protein kinase C (iota), In an eighth aspect the present invention consists in a method of screening a compound for human protein kinase C (iota) antagonist or agonist activity comprising exposing human protein kinase C (iota) produced by the method of the second aspect of the present invention to the compounds and assessing the activity of the human protein kinase C (iota).

The human protein kinase C (iota) may be isolated as described hereinafter or it may be synthesised, for example by cultivating a transformed host of the human protein kinase C (iota) in a suitable medium and thereafter isolating a recombinant protein of the human protein kinase (iota).

The regulation of the activity of human protein kinase C (iota) includes direct regulation of such activity, for example by antagonising the effect of human protein kinase C (iota), biologically active subpeptides of human protein kinase C (iota) or other human protein kinase C (iota) agonists. In addition, such regulation may be achieved indirectly, for example by antagonising the expression and/or synthesis of human protein kinase C (iota).

Suitable screening methods for identifying compounds which directly regulate the activity of human protein kinase C (iota) include conventional assay systems for determining such effects where the sequence of the protein is known, for example test compound may be admixed with a source of protein kinase C (iota) diacylglycerol and/or other activators and an ATP-generating system and the degree of phosphorylation of the protein substrate, for example histone.

A suitable source of protein kinase C (iota) includes cloned human protein kinase C (iota) expressed in a cell line or other expression vector system or isolated purified or partially purified protein kinase C (iota).

Suitable screening methods for identifying compounds which regulate the expression and/or synthesis of human protein kinase C (iota), include conventional methods for identifying the effect of such compounds upon proteins where the DNA sequence of the protein is known.

Suitable screening methods for identifying compounds which regulate the expression of human protein kinase C (iota) are those which involve the detection and/or determination of the amount of human protein kinase C (iota) or messenger RNA that encodes for protein kinase C (iota) or protein in the presence of the relevant test compound.

The detection and/or determination of the amount of human protein kinase C produced by a compound may be determined by conventional methods, for example by using an appropriate anti-body raised against human protein kinase C (iota).

The detection and/or determination of the amount of messenger RNA that encodes for human protein kinase C produced by a compound may also be determined by conventional methods, for example cells or a cell line such as HIT or RIN cells may be cultured in the presence of compound and the effect of such compound may then be determined by measuring the amount of mRNA produced, for example by Northern blot analysis.

The compound described in relation to the abovementioned methods includes proteins and non-protein compounds.

As indicated above the compounds which regulate the activity of human protein kinase C (iota) are considered to be of potential use in the treatment of diabetes.

Accordingly, in an alternative aspect, the present invention also provides a compound which regulates the activity of human protein kinase C (iota), for use as an active therapeutic substance, and in particular for use in the treatment of diabetes.

A compound which regulates the activity of human protein kinase C (iota) may be administered per se preferably, as a pharmaceutical composition also comprising a pharmaceutically acceptable carrier.

Accordingly, the present invention also provides a pharmaceutical composition comprising a compound which regulates the activity of human protein kinase C (iota) and a pharmaceutically acceptable carrier therefor.

As used herein the term pharmaceutically acceptable embraces compounds, compositions and ingredients for both human and veterinary use: for example the term pharmaceutically acceptable salt embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other convention adjuvant.

Typical carriers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit dose will contain an effective, non-toxic amount of the active ingredient. The active amounts of the particular compound chosen may be determined by conventional methods, for example by using methods disclosed in standard UK, European and U.S. Pharmacopoeias.

Generally the compositions will comprise compounds in the range of from 0.1 to 1000 mg, more usually 0.1 to 500 mg, and more especially 0.1 to 250 mg.

In the treatment and/or prophylaxis of diabetic humans, the compound of the invention may be taken in doses, such as those described above, one to six times a day in a manner such that the total daily dose for a 70 kg adult will generally be in the range of from 0.1 to 6000 mg, and more usually about 1 to 1500 mg.

In a further aspect, the present invention provides the use of a compound which regulates the activity of human protein kinase C (iota) for the manufacture of a medicament for the treatment and/or prophylaxis of hyperglycaemia.

The present invention also provides the use of a compound which regulates the activity of human protein kinase C (iota) for the manufacture of a medicament for the treatment and/or prophylaxis of hyperlipidaemia, hypertension, cardiovascular disease or certain eating disorders.

The following methods illustrate the invention but do not limit it any way.

EXPERIMENTAL PROCEDURES

PCR Amplification, Isolation and Characterization of a Novel PKC Sequence

Total RNA was extracted from each of the clonal insulin secreting cell lines HIT (hamster) and RINm5F (rat) using the guanidinium isothiocyanate procedure (24). Degenerate oligonucleotides corresponding to the regions of the known PKCs ($\alpha,\beta$, $\delta$, $\epsilon$, and $\zeta$) and containing a 5' EcoRI site and a 3' HindIII site were synthesized on an Applied Biosystems automatic DNA synthesizer. The sequences were as follows: 5'-GCTGACGAATTCGG$^{G}/_{C}$ATGTG$^{T}/_{C}$AA$^{G}/_{A}$GAA-3' (SEQ ID NO: 3) and 5'-CAGCACAAGCTT$^{C}$/G/$_{A}$G$^{C}/_{A}$C-CACCAGTC$^{T}/C/_{G}$AC-3'(SEQ ID NO: 4).

The oligonucleotides were then used for PCR with a Perkin Elmer-Cetus DNA thermal cycler. RNA (4–10 µg) was denatured by heating to 65° C. for 5 min, then reverse transcribed by incubation with 400 µM of each deoxynucleotide triphosphate, 0.5 µM of both oligonucleotide primers, 0.05 mM dithiothreitol in 50 mM KCl, 50 mM Tris-HCl pH 9.0, 1.5 mM MgCl$_2$ (PCR buffer) and 200 units moloney murine leukemia virus reverse transcriptase for 40 min at 37° C. The sample volume was then increased to 100 mL with PCR buffer, 0.5 units Tth enzyme added, and 50 µl light white mineral oil layered on top. The samples were heated for 5 min at 95° C. PCR conditions for 30 cycles were as follows: an increase over 1 min to 92° C. and then denaturation for 45 s, decrease over 1 min to 55° C. and annealing for 45 s, and an increase over 30 s to 72° C. and extension for 1 min. After the final extension step, the samples were held at 72° C. for 5 min.

Amplified DNA (20 µl) was removed and anlayzed by gel electrophoresis in 1% agarose and 3% NuSieve. Products that were approximately 170–220 bp in length were excised from the gel and were purified with Geneclean. DNA fragments were then digested with Hind III for 1 h at 37° C. and EcoRl for 1 h at 37° C., and the DNA purified with Geneclean again and eluted into 10 µl H$_2$O. Digested cDNA fragments were then subcloned into the M13mp19 vector and sequenced by the Sanger dideoxy chain-termination method (5). Sequencing reactions were analyzed on a 6% acrylamide, 7M urea gel, dried onto Whatman 3M paper, and exposed to x-ray film (Kodak X-OMAT AR5) for 16 h at room temperature overnight. Sequence analysis of the cDNA fragments generated from the PCR amplification identified a fragment with sequences common to other PKCs as determined by searches against the GenBank™ and EMBL databases.

Generation of a Full-length PKC cDNA Construct

A partial hamster cDNA clone with homologous sequence was next isolated by using the novel cDNA fragment, identified by PCR, to screen approximately $10^6$ plaques of a hamster HIT M2.2.2 cell cDNA library in lambda ZAP II plated on E. coli XL-1 Blue bacterial cells. Plaques were lifted onto 0.45 μM, 137 mm Hybond-N$^+$ nylon filters. DNA was denatured on the filters by a 5 min treatment with 0.5 M NaOH, 1.5 M NaCl, and neutralized with a 5 min incubation in 0.5M Tris, 1 mM EDTA, 1.5M NaCl (pH 7.2). Filters were rinsed in 2×SSC (0.3M NaCl, 0.03 M sodium citrate) and DNA was fixed on the filters with a 20 min incubation in 0.4M NaOH. Filters were prehybridized in 5×SSPE (1×SSPE=0.15M NaCl, 0.01M Na$_2$PO$_4$, 0.001M EDTA, pH 7.9), 5×Denhardt's solution (0.1%[w/v] BSA 0.1%[w/v] Ficoll, 0.1% [w/v] polyvinyllpyrollidone), 0.5% SDS and 2 mg/ml salmon sperm DNA at 65° C. for 1 h. The DNA fragment generated by PCR was labelled with $^{32}$P using a random hexanucleotide priming kit. Following hybridization to the radiolabeled cDNA fragment for 20 h at 60° C., filters were washed with 2×SSC, 0.1% SDS at 60° C. for 15 min twice, then with 1×SSC, 0.1% SDS, at 60° C. for 10 min twice, and exposed to Kodak X-OMAT AR5 film at −70° C. A pure phage isolate which hybridised to the radiolabeled cDNA fragment was obtained. The phagemid containing the hybridising cDNA was recovered and sequenced as described above. The clone (H17) represented a partial cDNA encoding the hamster homolog of putative new isoform of PKC.

The H17 cDNA was then used to screen approximately $10^6$ plaques of a human kidney cDNA library in lambda Max 1 plated on E. coli K802 cells. Two overlapping eDNA clones encoding the putative human PKC were isolated with hybridisation conditions as already described, except that filters were hybridised at 45° C. and washed with 2×SSC, 0.1% SDS at room temperature for 15 min, then 2×SSC, 0.1% SDS at 45° C. for 15 min, then 1×SSC, 0.1% SDS at 45° C. twice. Sequence analysis indicated that the first cDNA insert of 970 bp encoded the first 235 amino acids of the novel PKC and 264 bp of 5' untranslated sequence. The second cDNA insert of 1453 bp encoded amino acids 159–587 and 166 bp of 3' untranslated sequence. The overlapping sequence was identical. These regions were then spliced together at the common Nco I site at bp 578 and subcloned into a pAXNeORX expression vector, containing a neomycin resistance gene and the human beta actin promoter, to generate the PKCι/pAXNeoRX construct.

Northern Blot Analysis

Pancreatic islets were isolated by collagenase digestion and, in some instances, maintained in tissue culture for 72 h (4). Total RNA was prepared from rat tissues and various cell lines, as described above. RNA (10 mg) was run on a 1% agarose gel with 6% formamide, 0.2 M MOPS (pH 7.0), 50 mM Na acetate and 5 mM EDTA (ph 8.0) and transferred to Zeta Probe filters over-night in 10×SSC and fixed with 5 min incubation under UV light (312 nm). The oligonucleotide 5'-GGATGAAGCTTTGCCACTTTCCCTGGT-GTTCATTGC-3' (SEQ ID NO: 5), corresponding to a portion on the 3' untranslated region of PKCζ and labelled with γ-$^{32}$P using a kinase kit, was used for hybridization analysis of PKCζ. Filters were incubated in 1M NaCl, 0.05M Tris-HCl, 10% dextran sulphate, 1% SDS, 100 ng/ml salmon sperm DNA at 65° C. overnight; filters were washed sequentially with 2×SSC, 0.1% SDS for 15 min at room temperature, 1×SSC, 0.1% SDS for 30 min at 65° C., and 0.5×SSC, 0.1% SDS for 30 min at 65° C. The full-length PKCι cDNA construct (isolated from the PKCl/pAXNeoRX expression construct and labelled with [α-$^{32}$P]-dCTP by random priming) was used for hybridization analysis of PKCι. Filters were incubated in 50% formamide, 2×SSPE, 1% SDS, 10% Denhardt's solution, 10% dextran sulphate, 200 mg/ml yeast RNA, and 40 mg/ml poly A$^+$ RNA at 50° C. overnight; filters were washed with 2×SSC, 0.1% SDS for 10 min at room temperature, and then 1×SSC, 0.1% SDS for 15 min at 50° C.

Cell Culture and Transfections

RINm5F and HIT cell lines were cultured as previously described in RPMI 1640 medium (2,3). CHO Kl cells (American Type Culture Collection CCL 61) were maintained in 5% CO$_2$ in Dulbecco's modified Eagle's medium/ HamsF-12 with 2 mM glutamine, 100 international units/ml penicillin, streptomycin at 100 mg/ml, and 10% foetal calf serum, CHO Kl cells were stably transfected with the PKCι/pAXNeoRX construct or the pAXNeoRX vector alone using a modified calcium phosphate precipitate transfection method (6).

PKC Assays

Extracts were prepared from CHO Kl cells stably transfected with either the pAXneoRX or PKCι/pAXneoRX vector constructs. Extraction (approx. 15×10$^7$ cells) was by sonication in 1 ml ice-cold extraction buffer (20 mM MOPS, pH 7.5, 250 mM mannitol, 1 mM dithiothreitol, 1.2 mM EGTA, 20 mg/ml leupeptin and 0.2 mM phenylmethylsulfyl fluoride), for 6×20 s using a Branson Sonifier 250 and microtip at power setting 2 and 20% duty cycle. Cytosolic fractions were obtained by centrifugation at 100,000 g for 45 min at 4° C., and 10 ml samples were assayed for PKC activity after three-fold dilution in extraction buffer. The total assay volume was 50 ml, containing 24 mM MOPS, pH 7.5, 0.04% Triton X-100, 1 mM CaCl$_2$, 120 nM cyclic AMP-dependent protein kinase inhibitor peptide (rabbit sequence), 100 mM-[γ-$^{32}$P]ATP (100–200 c.p.m./pmol) and 5 mM magnesium acetate, in the absence or presence of 125 mg/ml phosphatidylserine and 2.5 mg/ml dioctanoylglycerol and either 5 mM PKC b modified pseudosubstrate peptide (19–31, Set25), 0.5 mg/ml histone HIIIS, 5 mM PKC ζ modified pseudosubstrate peptide (113–125, Ser119) or 0.1 mg/ml myelin basic protein as substrate. Lipids, at 5 mg/ml in chloroform/methanol (19:1), were dried under nitrogen and sonicated into 100 mM MOPS (pH 7.5) 1% Triton X-100 until clear before addition to the assay buffer. After 10 min at 30° C., assays were terminated with the addition of 10 ml of 150 mM unlabelled ATP, and samples were spotted onto Whatman P81 phospho-cellulose paper, washed with orthophosphoric acid and counted for Cerenkov radiation (7).

Immunoblotting

Cytosolic and particulate fractions, the equivalent of 50×10$^3$ CHO Kl cells and prepared as described above, were boiled with Laemmli sample buffer and subjected to SDS-PAGE using 10% gels. Protein was electroblotted onto nitrocellulose membrane (0.45 micron) and probed with 5 mg/ml rabbit anti-peptide antibody to PKCζ, followed by biotinylated donkey anti-rabbit antibody (1:50,000) and finally streptavidin-linked alkaline phosphatase (1:1000). Bands were visualized by incubation of the blotted membrane with 5-bromo-4-chloro-3-indoyl phospho-p-toluidine salt and p-nitro blue tetrazolium chloride.

Materials

All media and materials for tissue culture were obtained from Cytosystems, Sydney, Australia. Reverse transcriptase, kits for random priming, and PKCζ-specific oligonucleotide probes and antisera were supplied by Gibco BRL, Gaithersburg, Md. Zeta probe filters, nitrocellulose membranes and color reagents for immunoblotting were purchased from Bio-Rad Laboratories, Sydney, Australia. Hybond filters and all radiolabelled compounds came from Amersham Australia, Sydney, Australia The PKCζ pseudosubstrate peptide was made on an Applied Biosystems Synthesizer, whereas the PKCβ pseudosubstrate peptide was purchased from Auspep, Melbourne, Australia. Other substrates for PKC assays were from Sigma, St. Louis, Mo., as were lipid activators, protease inhibitors, white mineral oil and the cAMP-dependent kinase inhibitor. The pAXNeoRX expression vector and HIT cell cDNA library were generously provided by Pacific Biotechnology Pty Ltd, Sydney, Australia, and Dr Mark Magnuson, Vanderbilt University, Nashville, Tenn., respectively. The sources of other reagents were as follows: streptavidin-linked alkaline phosphatase, Kirkegaard & Perry Laboratories Inc. (Gaithersburg, Md.); biotin-linked secondary antibody, Jackson Immuno Research (Westgrove, Pa.); restriction enzymes and sequencing kits, Promega (Madison, Wis.); Tth enzyme, Toyobo (Japan); Geneclean, Bio 101 (San Diego, Calif.); and the human kidney cDNA library in lambda Max 1, Clontech (Palo Alto, Calif.).

RESULTS

Using PCR under the conditions defined in the Experimental Procedures section, and starting with mRNA extracted from the rat cell line, RINm5F, a novel sequence (Y2) was isolated. This was 120 nucleotides long (including primer bases) and displayed 79% identity with a corresponding region of rat PKCζ. An analogous sequence was isolated under identical conditions using mRNA derived from the hamster, insulin-secreting, HIT cell-line. Although Y2 was the only potential PKC sequence obtained using an annealing temperature of 55° C., under less stringent conditions (42°–50° C.) sequences corresponding to PKCS α, ε and ζ were also isolated from RINm5F cells and HIT cells.

The hamster Y2 sequence was subsequently used to screen a HIT cell cDNA library. This resulted in the isolation of a partial cDNA clone (H17) encoding the hamster homolog of a previously undescribed PKC isoform. The full-length sequence of the human homolog was then obtained from 2 overlapping clones, derived from a human kidney cDNA library screened with H17 as described under Experimental Procedures. This sequence (SEQ ID NO: 1) is shown in Table 1. It contains an open reading frame with two potential initiation sites at the positions designated −27 and 1

TABLE 1

Sequence Range: −264 to 1932

```
-264  CGGGGTGTCTTGGGCCCGGGCGGCTGTAGAGGCGGCGGCGCCTACGGGCAGTGGGAGGAGCCGCGCGGTT

-193  CCGGCTGCTCCGGCGAGGCGACCCTTGGGTCGGCGCTGCGGGCAGGTGGCAGGTAGGTGGCGGACGGCCG

-123  CGGTTCTCCGGCAAGCGCAGGCGGCGGAGTCCCCCACGGCGCCCGAAGCGCCCCCCCGCACCCCCGGCCT

-53  CCAGCGTTGAGGCGGGGGAGTGAGGAGATGCCGACCCAGAGGGACAGCAGCACCATGTCCCACACGGTCG        5
                                                              M   S   H   T   V

17  CAGGCGGCGGCAGCGGGGACCATTCCCACCAGGTCCGGGTGAAAGCCTACTACCGCGGGGATATCATGAT       29
       A   G   G   S   G   D   H   S   H   Q   V   R   V   K   A   Y   Y   R   G   D   I   M   I

87  AACACATTTTGAACCTTCCATCTCCTTTGAGGGCCTTTGCAATGAGGTTCGAGACATGTGTTCTTTTGAC       52
       T   H   F   E   P   S   I   S   F   E   G   L   C   N   E   V   R   D   M   C   S   F   D

157  AACGAACAGCTCTTCACCATGAAATGGATAGATGAGGAAGGAGACCCGTGTACAGTATCATCTCAGTTGG       75
       N   E   Q   L   F   I   M   K   W   I   D   E   E   G   D   P   C   T   V   S   S   Q   L

227  AGTTAGAAGAAGCCTTTAGACTTTATGAGCTAAACAAGGATTCTGAACTCTTGATTCATGTGTTCCCTTG       99
       E   L   E   E   A   F   R   L   Y   E   L   N   K   D   S   E   L   L   I   H   V   F   P   C

297  TGTACCAGAACGTCCTGGGATGCCTTGTCCAGGAGAAGATAAATCCATCTACCGTAGAGGTGCACGCCGC      122
       V   P   E   R   P   G   M   P   C   P   G   E   D   K   S   I   Y   R   R   G   A   R   R

367  TGGAGAAAGCTTTATTGTGCCAATGGCCACACTTTCCAAGCCAAGCGTTTCAACAGGCGTGCTCACTGTG      145
       W   R   K   L   Y   C   A   N   G   H   T   F   Q   A   K   R   F   N   R   R   A   H   C

437  CCATCTGCACAGACCGAATATGGGGACTTGGACGCCAAGGATATAAGTGCATCAACTGCAAACTCTTGGT      169
       A   I   C   T   D   R   I   W   G   L   G   R   Q   G   Y   K   C   I   N   C   K   L   L   V

507  TCATAAGAAGTGCCATAAACTCGTCACAATTGAATGTGGGCGGCATTCTTTGCCACAGGAACCAGTGATG      192
       H   K   K   C   H   K   L   V   T   I   E   C   G   R   H   S   L   P   Q   E   P   V   M

577  CCCATGGATCAGTCATCCATGCATTCTGACCATGCACAGACAGTAATTCCATATAATCCTTCAAGTCATG      215
       P   M   D   Q   S   S   M   H   S   D   H   A   Q   T   V   I   P   Y   N   P   S   S   H

647  AGAGTTTGGATCAAGTTGGTGAAGAAAAAGAGGCAATGAACACCAGGGAAAGTGGCAAAGCTTCATCCAG      239
       E   S   L   D   Q   V   G   E   E   K   E   A   M   N   T   R   E   S   G   K   A   S   S   S
```

TABLE 1-continued

Sequence Range: −264 to 1932

| | | |
|---|---|---|
| 717 | TCTAGGTCTTCAGGATTTTGATTTGCTCCGGGTAATAGGAAGAGGAAGTTATGCCAAAGTACTGTTGGTT<br>L  G  L  Q  D  F  D  L  L  R  V  I  G  R  G  S  Y  A  K  V  L  L  V | 262 |
| 787 | CGATTAAAAAAAACAGATCGTATTTATGCAATGAAAGTTGTGAAAAAAGAGCTTGTTAATGATGATGAGG<br>R  L  K  K  T  D  R  I  Y  A  M  K  V  V  K  K  E  L  V  N  D  D  E | 285 |
| 857 | ATATTGATTGGGTACAGACAGAGAAGCATGTGTTTGAGCAGGCATCCAATCATCCTTTCCTTGTTGGGCT<br>D  I  D  W  V  Q  T  E  K  H  V  F  E  Q  A  S  N  H  P  F  L  V  G  L | 309 |
| 927 | GCATTCTTGCTTTCAGACAGAAAGCAGATTGTTCTTTGTTATAGAGTATGTAAATGGAGGAGACCTAATG<br>H  S  C  F  Q  T  E  S  R  L  F  F  V  I  E  Y  V  N  G  G  D  L  M | 332 |
| 997 | TTTCATATGCAGCGACAAAGAAAACTTCCTGAAGAACATGCCAGATTTTACTCTGCAGAAATCAGTCTAG<br>F  H  M  Q  R  Q  R  K  L  P  E  E  H  A  R  F  Y  S  A  E  I  S  L | 355 |
| 1067 | CATTAAATTATCTTCATGAGCGAGGGATAATTTATAGAGATTTGAAACTGGACAATGTATTACTGGACTC<br>A  L  N  Y  L  H  E  R  G  I  I  Y  R  D  L  K  L  D  N  V  L  L  D  S | 379 |
| 1137 | TGAAGGCCACATTAAACTCACTGACTACGGCATGTGTAAGGAAGGATTACGGCCAGGAGATACAACCAGC<br>E  G  H  I  K  L  T  D  Y  G  M  C  K  E  G  L  R  P  G  D  T  T  S | 402 |
| 1207 | ACTTTCTGTGGTACTCCTAATTACATTGCTCCTGAAATTTTAAGAGGAGAAGATTATGGTTTCAGTGTTG<br>T  F  C  G  T  P  N  Y  I  A  P  E  I  L  R  G  E  D  Y  G  F  S  V | 425 |
| 1277 | ACTGGTGGGCTCTTGGAGTGCTCATGTTTGAGATGATGGCAGGAAGGTCTCCATTTGATATTGTTGGGAG<br>D  W  W  A  L  G  V  L  M  F  E  M  M  A  G  R  S  P  F  D  I  V  G  S | 449 |
| 1347 | CTCCGATAACCCTGACCAGAACACAGAGGATTATCTCTTCCAAGTTATTTTGGAAAAACAAATTCGCATA<br>S  D  N  P  D  Q  N  T  E  D  Y  L  F  Q  V  I  L  E  K  Q  I  R  I | 472 |
| 1417 | CCACGTTCT CTGTCTGTAAAAGCTGCAAGTGTTCTGAAGAGTTTTCTTAATAAGGACCCTAAGGAACGAT<br>P  R  S  L  S  V  K  A  A  S  V  L  K  S  F  L  N  K  D  P  K  E  R | 495 |
| 1487 | TGGGTTGTCATCCTCAAACAGGATTTGCTGATATTCAGGGACACCCGTTCTTCCGAAATGTTGATTGGGA<br>L  G  C  H  P  Q  T  G  F  A  D  I  Q  G  H  P  F  F  R  N  V  D  W  D | 519 |
| 1557 | TATGATGGAGCAAAAACAGGTGGTACCTCCCTTTAAACCAAATATTTCTGGGGAATTTGGTTTGGACAAC<br>M  M  E  Q  K  Q  V  V  P  P  F  K  P  N  I  S  G  E  F  G  L  D  N | 542 |
| 1627 | TTTGATTCTCAGTTTACTAATGAACCTGTCCAGCTCACTCCAGATGACGATGACATTGTGAGGAAGATTG<br>F  D  S  Q  F  T  N  E  P  V  Q  L  T  P  D  D  D  D  I  V  R  K  I | 565 |
| 1697 | ATCAGTCTGAATTTGAAGGTTTTGAGTATATCAATCCTCTTTTGATGTCTGCAGAAGAATGTGTCTGATC<br>D  Q  S  E  F  E  G  F  E  Y  I  N  P  L  L  M  S  A  E  E  C  V  * | 587 |
| 1767 | CTCATTTTTCAACCATGTATTCTACTCATGTTGCCATTTAATGCATGGATAAACTTGCTGCAAGCCTGGA | |
| 1837 | TACAATTAACCATTTTATATTTGCCACCTACAAAAAAAACACCCAATATCTTCTCTTGTAGACTATATGAA | |
| 1907 | TCAATTATTACATCTCGACCCGGAAT  1932 | | respectively. The latter ATG is more likely to be the translational start site, since the nucleotides GCACC, found immediately before it, are a much better match with the Kozak (8) consensus sequence $CC^A/_GCC$ for initiation of translation, than the AGGAG sequence which precedes the alternative site. Also displayed in Table 1. is the deduced amino acid sequence of the 587 amino acid protein, human PKCι.

Comparison of the sequence of human PKCι with those of the other PKC isoforms revealed two highly conserved regions: a cystsine-rich area in the regulatory domain and the entire catalytic portion. The percent identity between PKCι and the other PKCs in these regions is shown in Table 2. By far the greatest similarity is to PKCζ. Indeed these 2 isoforms show limited homology even in the V1 region (58%) and, to a lesser extent, the V3 region (32%) resulting in an overall identity of 72%. They share an almost identical pseudosubstrate domain in the C1 region, and possess a single zinc finger-like motif, $C-X_2-C-X_{13(14)}-C-X_2-C-X_7-C-X_7-C$ (9). This sequence, although highly conserved across the entire PKC family, exists as a tandem repeat in all isoforms except ι and ζ (Table 2). PKCι also lacked the calcium-binding C2 domain which is present in the classical, but not novel or atypical PKC isoforms. The catalytic region of PKCι is highly homologous to those of the other PKCs (Table 2) and shares a number of sequence motifs in common with them. These include the triplets A-X-K at residues 272–274, and A-P-E (412–414), both highly conserved in all protein kinases, and the D-L-K-X-X-N sequence (369–374) which is characteristic of serine-threonine kinases (10). Interestingly, two substitutions in PKCζ, of residues highly conserved in other kinases, are also present in PKCι. The first is the D-Y-G triplet at position 420–422 which occurs as a D-F-G sequence in almost all other protein kinases (10). The second is the substitution of alanine for the third glycine residue in the ATP-binding domain (G-X-G-X-X-G-X-V). Another region of PKCι worth highlighting is that corresponding to residues 446–454. This contains an additional 2 amino acids as compared to the equivalent region in PKCζ, which is itself a 7 residue insertion not found in the other PKC isoforms.

TABLE 2

Amino acid identities between PKCι and
the other PKC isoforms in conserved domains.

| | Sequence Identity | |
|---|---|---|
| PKC isoform | 1st Zinc Finger | Catalytic Domain % |
| α | 40 | 50 |
| β | 40 | 52 |
| γ | 39 | 48 |
| δ | 32 | 48 |
| θ | 34 | 44 |
| ε | 39 | 53 |
| η | 38 | 51 |
| ζ | 77 | 84 |

The tissue distribution of PKCι was determined by Northern blot analysis and compared with that of PKCζ. As previously described, the latter existed as 2 transcripts of approximately 2.4 and 4.4 kb and was expressed in brain, and to a lesser extent, in lung, kidney and testis (1,11). There was also detectable expression, especially of the 2.4 kb transcript, in freshly isolated or 48 h cultured islets, and in the two insulin-secreting cell lines. In contrast, the probe for PKCι hybridized to a single transcript of 4.6 kb, slightly bigger than the larger of the two PKCζ bands. PKCι appeared to be widely expressed, but most notably in lung and brain, followed by kidney. The RINm5F and HIT cell lines also displayed obvious hybridization, with fainter bands appearing in the islet extracts.

In order to examine the heterologous expression of PKCι, we took advantage of the fact that the C-terminal ends of the human PKCι and PKCζ are highly conserved. Rat PKCζ contains an alanine for threonine substitution at position 588, making it even more homologous to human PKCι. This is noteworthy because the 16 C-terminal. residues of rat PKCζ have been widely used to generate antisera purportedly specific to PKCζ (1). However it might be predicted that such antisera would also crossreact with PKCι. In these experiments CHO Kl cells were transfected with a construct encoding human PKCι since Northern analysis revealed that these cells did not appear to express this isoform endogenously (not shown). Mowever, they did contain PKCζ, which was detected as a 74 kDa protein. The antisera also identified a protein of approximately 65 kDa, which was only present in PKCι-transfected CHO Kl cells, but not in those transfected with vector alone. This is consistent with the deduced molecular weight of 67 kDa for PKCι. In contrast to PKCζ, the lower band was slightly more abundant in the particulate fraction as opposed to the high-speed supernatant of cell extracts.

The functional activity of PKCι was next examined using the CHO Kl cell lines described above. In these studies kinase activity was determined as the ability of cell extracts to phos-phorylate a number of potential substrates: PKC-specific activity was assessed in the presence of $Ca^{2+}$, phosphatidylserine and dioctanoylglycerol as compared to basal (non-PKC) activity due to $Ca^{2+}$ alone. CHO Kl cells not expressing PKCι displayed a high endogenous PKC activity, especially using PKCb modified pseudosubstrate as a phosphate acceptor (results not shown). This background activity was less pronounced using substrates which were less specific for the classical PKC isoforms. Thus with Histone IIIs and PKCζ modified pseudosubstrate, stimulated PKC activity was approximately double the basal level, whereas with myelin basic protein it was only slightly enhanced. In cells transfected with the PKCι/pAXNeoRX construct, basal kinase activity was unaltered. Moreover total PKC activity against Histone IIIs and PKCζ modified pseudosubstrate was only slightly, and non-significantly, augmented. In marked contrast, the cells expressing PKCι showed a doubling in PKC activity when myelin basic protein was used as the substrate. This provides direct evidence that PKCι is a phospholipid-dependent protein kinase, but probably one with a different substrate profile to the previously defined, classical or novel PKC isoforms. Expression of nPKCι in E. coli, purification and preparation of antibodies.

PKCι was expressed by insertion of the DNA sequence into the pMal™-c vector (New England Biolabs) and expressed in E. coli as a fusion protein, with maltose binding protein (MBP) and Factor Xa cleavage site at the N-terminus.

The fusion protein was purified by DEAE-cellulose chromatography followed by affinity chromatography using amylose resin (New England Biolabs), and the preparation concentrated by ultrafiltration. Factor Xa was used to cleave MBP from PKCι, and the kinase isolated by further affinity chromatography to remove MBP, and again concentrated.

To generate a polyclonal antiserum against PKCι, the purified enzyme (500 μg in 500 μl saline plus 500 μl Freund's complete adjuvant), was injected into a rabbit. Three booster injections (300 μg in 500 ml saline with 500 μl Freund's incomplete adjuvant) were given at two-weekly intervals, and serum harvested after 10 weeks.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Ono, Y., Fujii, T., Ogita, K., Kikkawa, U., Igarashi, K., and Nishizuka, Y. (1989) Proc Natl Acad Sci U.S.A. 86, 3099–103.

2. Regazzi, R., Li, G., Desbusses, J., and Wollheim, C. B. (1990) J. Biol. Chem. 265, 15003–15009.

3. Wollheim, C. B., and Biden, T. J. (1986) J. Biol. Chem. 261, 8314–83319.

4. Biden, T. J., Peter-Riesch, B., Schlegel, W. and Wollheim, C. B. (1987) J. Biol. Chem. 262, 3567–3571.

5. Sanger, F., Miklen, S., and Coulson, A. R. (1977) Proc. Natl. Acad. Sci. U.S.A. 74, 5463–5467.

6. Sambrook, J., Fritsch, E. F., and Maniatis, T. (1989) Molecular Cloning: A Laboratory Manuel Cold Spring Harbor Press, 2nd ed.

7. Glass, D. B., Masaracchia, R. A., Feramisco, J. R., and Kemp, B. E. (1978) Anal. Biochem. 87, 566–575.

8. Kozak, M. (1984) Nucleic Acid. Res. 12, 857–872.

9. Hubbard, S. R., Bishop, W. R., Kirschmeier, P., George, S. J., Cramer, S. P., and Hendrickson, W. A. (1991) Science 254, 1776–1779.

10. Hanks, S. K., Quinn, A. M., and Hunter T. (1988) Science 241, 42–52.

11. Goodnight, J., Kazanietz, M. G., Mushinski, J. F., and Mischak, H. (1992) Gene 122, 305–311.

We claim:

1. An isolated DNA molecule which encodes human protein kinase C (ita), said DNA molecule encoding the amino acid sequence as shown in SEQ ID NO: 2.

2. An isolated DNA molecule which encodes human protein kinase C (iota), said DNA molecule having the nucleotide sequence as shown in SEQ ID NO: 1.

3. A veactor including the DNA molecule as claimed in claim 1.

4. A cell transformed with the vector as claimed in claim 3.

5. A cell as claimed in claim 4 in which the cell is a mammalian or insect cell.

6. A method of producing protein kinase C (iota) comprising culturing the cell as claimed in claim 4 under conditions which allow expression of the DNA molecule encoding human protein kinase C (iota) and recovering the expressed protein kinase C (iota).

* * * * *

UNITED STATES PATENT AND TRADEMARK OFFICE
CERTIFICATE OF CORRECTION

PATENT NO. : 5,595,902
DATED : January 21, 1997
INVENTOR(S) : Trevor J. Biden et al.

It is certified that error appears in the above-indentified patent and that said Letters Patent is hereby corrected as shown below:

<u>In the Claims:</u>  Col. 21, line 51 (claim 1), "(ita)" should be -- (iota) --.

Signed and Sealed this

Twentieth Day of January, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2196 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 265..2025

( x i ) SEQUENCE DESCRIPTION: SEQ ID NO:1:

```
CGGGGTGTCT TGGGCCCGGG CGGCTGTAGA GGCGGCGGCG CCTACGGGCA GTGGGAGGAG      60

CCGCGCGGTT CCGGCTGCTC CGGCGAGGCG ACCCTTGGGT CGGCGCTGCG GCAGGTGGC      120

AGGTAGGTGG CGGACGGCCG CGGTTCTCCG GCAAGCGCAG GCGGCGGAGT CCCCCCACGG     180

CGCCCGAAGC GCCCCCCCGC ACCCCGCCT  CCAGCGTTGA GGCGGGGGAG TGAGGAGATG     240

CCGACCCAGA GGGACAGCAG CACC ATG TCC CAC ACG GTC GCA GGC GGC GGC        291
                            Met Ser His Thr Val Ala Gly Gly Gly
                            1               5

AGC GGG GAC CAT TCC CAC CAG GTC CGG GTG AAA GCC TAC TAC CGC GGG       339
Ser Gly Asp His Ser His Gln Val Arg Val Lys Ala Tyr Tyr Arg Gly
10              15                  20                  25

GAT ATC ATG ATA ACA CAT TTT GAA CCT TCC ATC TCC TTT GAG GGC CTT       387
Asp Ile Met Ile Thr His Phe Glu Pro Ser Ile Ser Phe Glu Gly Leu
        30                  35                  40

TGC AAT GAG GTT CGA GAC ATG TGT TCT TTT GAC AAC GAA CAG CTC TTC       435
Cys Asn Glu Val Arg Asp Met Cys Ser Phe Asp Asn Glu Gln Leu Phe
                45                  50                  55

ACC ATG AAA TGG ATA GAT GAG GAA GGA GAC CCG TGT ACA GTA TCA TCT       483
Thr Met Lys Trp Ile Asp Glu Glu Gly Asp Pro Cys Thr Val Ser Ser
            60                  65                  70

CAG TTG GAG TTA GAA GAA GCC TTT AGA CTT TAT GAG CTA AAC AAG GAT       531
Gln Leu Glu Leu Glu Glu Ala Phe Arg Leu Tyr Glu Leu Asn Lys Asp
        75                  80                  85

TCT GAA CTC TTG ATT CAT GTG TTC CCT TGT GTA CCA GAA CGT CCT GGG       579
Ser Glu Leu Leu Ile His Val Phe Pro Cys Val Pro Glu Arg Pro Gly
90                  95                  100                 105

ATG CCT TGT CCA GGA GAA GAT AAA TCC ATC TAC CGT AGA GGT GCA CGC       627
Met Pro Cys Pro Gly Glu Asp Lys Ser Ile Tyr Arg Arg Gly Ala Arg
                110                 115                 120

CGC TGG AGA AAG CTT TAT TGT GCC AAT GGC CAC ACT TTC CAA GCC AAG       675
Arg Trp Arg Lys Leu Tyr Cys Ala Asn Gly His Thr Phe Gln Ala Lys
            125                 130                 135

CGT TTC AAC AGG CGT GCT CAC TGT GCC ATC TGC ACA GAC CGA ATA TGG       723
Arg Phe Asn Arg Arg Ala His Cys Ala Ile Cys Thr Asp Arg Ile Trp
        140                 145                 150

GGA CTT GGA CGC CAA GGA TAT AAG TGC ATC AAC TGC AAA CTC TTG GTT       771
Gly Leu Gly Arg Gln Gly Tyr Lys Cys Ile Asn Cys Lys Leu Leu Val
    155                 160                 165
```

| | | | | | | | | | | | | | | | | |
|---|---|---|---|---|---|---|---|---|---|---|---|---|---|---|---|---|
| CAT | AAG | AAG | TGC | CAT | AAA | CTC | GTC | ACA | ATT | GAA | TGT | GGG | CGG | CAT | TCT | 819 |
| His | Lys | Lys | Cys | His | Lys | Leu | Val | Thr | Ile | Glu | Cys | Gly | Arg | His | Ser | |
| 170 | | | | 175 | | | | | 180 | | | | | 185 | | |
| TTG | CCA | CAG | GAA | CCA | GTG | ATG | CCC | ATG | GAT | CAG | TCA | TCC | ATG | CAT | TCT | 867 |
| Leu | Pro | Gln | Glu | Pro | Val | Met | Pro | Met | Asp | Gln | Ser | Ser | Met | His | Ser | |
| | | | | 190 | | | | 195 | | | | | 200 | | | |
| GAC | CAT | GCA | CAG | ACA | GTA | ATT | CCA | TAT | AAT | CCT | TCA | AGT | CAT | GAG | AGT | 915 |
| Asp | His | Ala | Gln | Thr | Val | Ile | Pro | Tyr | Asn | Pro | Ser | Ser | His | Glu | Ser | |
| | | | 205 | | | | | 210 | | | | | 215 | | | |
| TTG | GAT | CAA | GTT | GGT | GAA | GAA | AAA | GAG | GCA | ATG | AAC | ACC | AGG | GAA | AGT | 963 |
| Leu | Asp | Gln | Val | Gly | Glu | Glu | Lys | Glu | Ala | Met | Asn | Thr | Arg | Glu | Ser | |
| | | 220 | | | | | 225 | | | | | 230 | | | | |
| GGC | AAA | GCT | TCA | TCC | AGT | CTA | GGT | CTT | CAG | GAT | TTT | GAT | TTG | CTC | CGG | 1011 |
| Gly | Lys | Ala | Ser | Ser | Ser | Leu | Gly | Leu | Gln | Asp | Phe | Asp | Leu | Leu | Arg | |
| | 235 | | | | | 240 | | | | | 245 | | | | | |
| GTA | ATA | GGA | AGA | GGA | AGT | TAT | GCC | AAA | GTA | CTG | TTG | GTT | CGA | TTA | AAA | 1059 |
| Val | Ile | Gly | Arg | Gly | Ser | Tyr | Ala | Lys | Val | Leu | Leu | Val | Arg | Leu | Lys | |
| 250 | | | | | 255 | | | | | 260 | | | | | 265 | |
| AAA | ACA | GAT | CGT | ATT | TAT | GCA | ATG | AAA | GTT | GTG | AAA | AAA | GAG | CTT | GTT | 1107 |
| Lys | Thr | Asp | Arg | Ile | Tyr | Ala | Met | Lys | Val | Val | Lys | Lys | Glu | Leu | Val | |
| | | | | 270 | | | | | 275 | | | | | 280 | | |
| AAT | GAT | GAT | GAG | GAT | ATT | GAT | TGG | GTA | CAG | ACA | GAG | AAG | CAT | GTG | TTT | 1155 |
| Asn | Asp | Asp | Glu | Asp | Ile | Asp | Trp | Val | Gln | Thr | Glu | Lys | His | Val | Phe | |
| | | | 285 | | | | | 290 | | | | | 295 | | | |
| GAG | CAG | GCA | TCC | AAT | CAT | CCT | TTC | CTT | GTT | GGG | CTG | CAT | TCT | TGC | TTT | 1203 |
| Glu | Gln | Ala | Ser | Asn | His | Pro | Phe | Leu | Val | Gly | Leu | His | Ser | Cys | Phe | |
| | | 300 | | | | | 305 | | | | | 310 | | | | |
| CAG | ACA | GAA | AGC | AGA | TTG | TTC | TTT | GTT | ATA | GAG | TAT | GTA | AAT | GGA | GGA | 1251 |
| Gln | Thr | Glu | Ser | Arg | Leu | Phe | Phe | Val | Ile | Glu | Tyr | Val | Asn | Gly | Gly | |
| | 315 | | | | | 320 | | | | | 325 | | | | | |
| GAC | CTA | ATG | TTT | CAT | ATG | CAG | CGA | CAA | AGA | AAA | CTT | CCT | GAA | GAA | CAT | 1299 |
| Asp | Leu | Met | Phe | His | Met | Gln | Arg | Gln | Arg | Lys | Leu | Pro | Glu | Glu | His | |
| 330 | | | | | 335 | | | | | 340 | | | | | 345 | |
| GCC | AGA | TTT | TAC | TCT | GCA | GAA | ATC | AGT | CTA | GCA | TTA | AAT | TAT | CTT | CAT | 1347 |
| Ala | Arg | Phe | Tyr | Ser | Ala | Glu | Ile | Ser | Leu | Ala | Leu | Asn | Tyr | Leu | His | |
| | | | | 350 | | | | | 355 | | | | | 360 | | |
| GAG | CGA | GGG | ATA | ATT | TAT | AGA | GAT | TTG | AAA | CTG | GAC | AAT | GTA | TTA | CTG | 1395 |
| Glu | Arg | Gly | Ile | Ile | Tyr | Arg | Asp | Leu | Lys | Leu | Asp | Asn | Val | Leu | Leu | |
| | | | 365 | | | | | 370 | | | | | 375 | | | |
| GAC | TCT | GAA | GGC | CAC | ATT | AAA | CTC | ACT | GAC | TAC | GGC | ATG | TGT | AAG | GAA | 1443 |
| Asp | Ser | Glu | Gly | His | Ile | Lys | Leu | Thr | Asp | Tyr | Gly | Met | Cys | Lys | Glu | |
| | | | 380 | | | | | 385 | | | | | 390 | | | |
| GGA | TTA | CGG | CCA | GGA | GAT | ACA | ACC | AGC | ACT | TTC | TGT | GGT | ACT | CCT | AAT | 1491 |
| Gly | Leu | Arg | Pro | Gly | Asp | Thr | Thr | Ser | Thr | Phe | Cys | Gly | Thr | Pro | Asn | |
| | 395 | | | | | 400 | | | | | 405 | | | | | |
| TAC | ATT | GCT | CCT | GAA | ATT | TTA | AGA | GGA | GAA | GAT | TAT | GGT | TTC | AGT | GTT | 1539 |
| Tyr | Ile | Ala | Pro | Glu | Ile | Leu | Arg | Gly | Glu | Asp | Tyr | Gly | Phe | Ser | Val | |
| 410 | | | | | 415 | | | | | 420 | | | | | 425 | |
| GAC | TGG | TGG | GCT | CTT | GGA | GTG | CTC | ATG | TTT | GAG | ATG | ATG | GCA | GGA | AGG | 1587 |
| Asp | Trp | Trp | Ala | Leu | Gly | Val | Leu | Met | Phe | Glu | Met | Met | Ala | Gly | Arg | |
| | | | | 430 | | | | 435 | | | | | 440 | | | |
| TCT | CCA | TTT | GAT | ATT | GTT | GGG | AGC | TCC | GAT | AAC | CCT | GAC | CAG | AAC | ACA | 1635 |
| Ser | Pro | Phe | Asp | Ile | Val | Gly | Ser | Ser | Asp | Asn | Pro | Asp | Gln | Asn | Thr | |
| | | | 445 | | | | 450 | | | | | 455 | | | | |
| GAG | GAT | TAT | CTC | TTC | CAA | GTT | ATT | TTG | GAA | AAA | CAA | ATT | CGC | ATA | CCA | 1683 |
| Glu | Asp | Tyr | Leu | Phe | Gln | Val | Ile | Leu | Glu | Lys | Gln | Ile | Arg | Ile | Pro | |
| | | 460 | | | | 465 | | | | | 470 | | | | | |
| CGT | TCT | CTG | TCT | GTA | AAA | GCT | GCA | AGT | GTT | CTG | AAG | AGT | TTT | CTT | AAT | 1731 |
| Arg | Ser | Leu | Ser | Val | Lys | Ala | Ala | Ser | Val | Leu | Lys | Ser | Phe | Leu | Asn | |
| | 475 | | | | 480 | | | | | 485 | | | | | | |

-continued

| | | | | | | | | | | | | | | | | |
|---|---|---|---|---|---|---|---|---|---|---|---|---|---|---|---|---|
| AAG | GAC | CCT | AAG | GAA | CGA | TTG | GGT | TGT | CAT | CCT | CAA | ACA | GGA | TTT | GCT | 1779 |
| Lys | Asp | Pro | Lys | Glu | Arg | Leu | Gly | Cys | His | Pro | Gln | Thr | Gly | Phe | Ala | |
| 490 | | | | 495 | | | | | 500 | | | | | | 505 | |
| GAT | ATT | CAG | GGA | CAC | CCG | TTC | TTC | CGA | AAT | GTT | GAT | TGG | GAT | ATG | ATG | 1827 |
| Asp | Ile | Gln | Gly | His | Pro | Phe | Phe | Arg | Asn | Val | Asp | Trp | Asp | Met | Met | |
| | | | | 510 | | | | | 515 | | | | | 520 | | |
| GAG | CAA | AAA | CAG | GTG | GTA | CCT | CCC | TTT | AAA | CCA | AAT | ATT | TCT | GGG | GAA | 1875 |
| Glu | Gln | Lys | Gln | Val | Val | Pro | Pro | Phe | Lys | Pro | Asn | Ile | Ser | Gly | Glu | |
| | | | 525 | | | | | 530 | | | | | 535 | | | |
| TTT | GGT | TTG | GAC | AAC | TTT | GAT | TCT | CAG | TTT | ACT | AAT | GAA | CCT | GTC | CAG | 1923 |
| Phe | Gly | Leu | Asp | Asn | Phe | Asp | Ser | Gln | Phe | Thr | Asn | Glu | Pro | Val | Gln | |
| | | | 540 | | | | 545 | | | | | 550 | | | | |
| CTC | ACT | CCA | GAT | GAC | GAT | GAC | ATT | GTG | AGG | AAG | ATT | GAT | CAG | TCT | GAA | 1971 |
| Leu | Thr | Pro | Asp | Asp | Asp | Asp | Ile | Val | Arg | Lys | Ile | Asp | Gln | Ser | Glu | |
| | | 555 | | | | | 560 | | | | 565 | | | | | |
| TTT | GAA | GGT | TTT | GAG | TAT | ATC | AAT | CCT | CTT | TTG | ATG | TCT | GCA | GAA | GAG | 2019 |
| Phe | Glu | Gly | Phe | Glu | Tyr | Ile | Asn | Pro | Leu | Leu | Met | Ser | Ala | Glu | Glu | |
| 570 | | | | | 575 | | | | | 580 | | | | | 585 | |
| TGT | GTC | TGATCCTCAT | | TTTTCAACCA | | TGTATTCTAC | | TCATGTTGCC | | ATTTAATGCA | | | | | | 2075 |
| Cys | Val | | | | | | | | | | | | | | | |

TGGATAAACT TGCTGCAAGC CTGGATACAA TTAACCATTT TATATTTGCC ACCTACAAAA 2135

AAACACCCAA TATCTTCTCT TGTAGACTAT ATGAATCAAT TATTACATCT CGACCCGGAA 2195

T 2196

( 2 ) INFORMATION FOR SEQ ID NO:2:

( i ) SEQUENCE CHARACTERISTICS:
        ( A ) LENGTH: 587 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | His | Thr | Val | Ala | Gly | Gly | Gly | Ser | Gly | Asp | His | Ser | His | Gln |
| 1 | | | | 5 | | | | | 10 | | | | | 15 | |
| Val | Arg | Val | Lys | Ala | Tyr | Tyr | Arg | Gly | Asp | Ile | Met | Ile | Thr | His | Phe |
| | | | 20 | | | | | 25 | | | | | 30 | | |
| Glu | Pro | Ser | Ile | Ser | Phe | Glu | Gly | Leu | Cys | Asn | Glu | Val | Arg | Asp | Met |
| | | | 35 | | | | 40 | | | | | 45 | | | |
| Cys | Ser | Phe | Asp | Asn | Glu | Gln | Leu | Phe | Thr | Met | Lys | Trp | Ile | Asp | Glu |
| | | 50 | | | | | 55 | | | | | 60 | | | |
| Glu | Gly | Asp | Pro | Cys | Thr | Val | Ser | Ser | Gln | Leu | Glu | Leu | Glu | Glu | Ala |
| 65 | | | | | 70 | | | | | 75 | | | | | 80 | |
| Phe | Arg | Leu | Tyr | Glu | Leu | Asn | Lys | Asp | Ser | Glu | Leu | Leu | Ile | His | Val |
| | | | | 85 | | | | | 90 | | | | | 95 | |
| Phe | Pro | Cys | Val | Pro | Glu | Arg | Pro | Gly | Met | Pro | Cys | Pro | Gly | Glu | Asp |
| | | | | 100 | | | | | 105 | | | | | 110 | |
| Lys | Ser | Ile | Tyr | Arg | Arg | Gly | Ala | Arg | Arg | Trp | Arg | Lys | Leu | Tyr | Cys |
| | | | 115 | | | | | 120 | | | | | 125 | | |
| Ala | Asn | Gly | His | Thr | Phe | Gln | Ala | Lys | Arg | Phe | Asn | Arg | Arg | Ala | His |
| | 130 | | | | | 135 | | | | | 140 | | | | | |
| Cys | Ala | Ile | Cys | Thr | Asp | Arg | Ile | Trp | Gly | Leu | Gly | Arg | Gln | Gly | Tyr |
| 145 | | | | | 150 | | | | | 155 | | | | | 160 | |
| Lys | Cys | Ile | Asn | Cys | Lys | Leu | Leu | Val | His | Lys | Lys | Cys | His | Lys | Leu |
| | | | | 165 | | | | | 170 | | | | | 175 | |
| Val | Thr | Ile | Glu | Cys | Gly | Arg | His | Ser | Leu | Pro | Gln | Glu | Pro | Val | Met |
| | | | 180 | | | | | 185 | | | | | 190 | | |

Pro Met Asp Gln Ser Ser Met His Ser Asp His Ala Gln Thr Val Ile
    195                 200                 205

Pro Tyr Asn Pro Ser Ser His Glu Ser Leu Asp Gln Val Gly Glu Glu
    210                 215                 220

Lys Glu Ala Met Asn Thr Arg Glu Ser Gly Lys Ala Ser Ser Ser Leu
225                 230                 235                 240

Gly Leu Gln Asp Phe Asp Leu Leu Arg Val Ile Gly Arg Gly Ser Tyr
                245                 250                 255

Ala Lys Val Leu Leu Val Arg Leu Lys Thr Asp Arg Ile Tyr Ala
                260                 265                 270

Met Lys Val Val Lys Lys Glu Leu Val Asn Asp Asp Glu Asp Ile Asp
        275                 280                 285

Trp Val Gln Thr Glu Lys His Val Phe Glu Gln Ala Ser Asn His Pro
    290                 295                 300

Phe Leu Val Gly Leu His Ser Cys Phe Gln Thr Glu Ser Arg Leu Phe
305                 310                 315                 320

Phe Val Ile Glu Tyr Val Asn Gly Gly Asp Leu Met Phe His Met Gln
                325                 330                 335

Arg Gln Arg Lys Leu Pro Glu Glu His Ala Arg Phe Tyr Ser Ala Glu
            340                 345                 350

Ile Ser Leu Ala Leu Asn Tyr Leu His Glu Arg Gly Ile Ile Tyr Arg
        355                 360                 365

Asp Leu Lys Leu Asp Asn Val Leu Leu Asp Ser Glu Gly His Ile Lys
    370                 375                 380

Leu Thr Asp Tyr Gly Met Cys Lys Glu Gly Leu Arg Pro Gly Asp Thr
385                 390                 395                 400

Thr Ser Thr Phe Cys Gly Thr Pro Asn Tyr Ile Ala Pro Glu Ile Leu
                405                 410                 415

Arg Gly Glu Asp Tyr Gly Phe Ser Val Asp Trp Trp Ala Leu Gly Val
            420                 425                 430

Leu Met Phe Glu Met Met Ala Gly Arg Ser Pro Phe Asp Ile Val Gly
        435                 440                 445

Ser Ser Asp Asn Pro Asp Gln Asn Thr Glu Asp Tyr Leu Phe Gln Val
    450                 455                 460

Ile Leu Glu Lys Gln Ile Arg Ile Pro Arg Ser Leu Ser Val Lys Ala
465                 470                 475                 480

Ala Ser Val Leu Lys Ser Phe Leu Asn Lys Asp Pro Lys Glu Arg Leu
                485                 490                 495

Gly Cys His Pro Gln Thr Gly Phe Ala Asp Ile Gln Gly His Pro Phe
            500                 505                 510

Phe Arg Asn Val Asp Trp Asp Met Met Glu Gln Lys Gln Val Val Pro
        515                 520                 525

Pro Phe Lys Pro Asn Ile Ser Gly Glu Phe Gly Leu Asp Asn Phe Asp
    530                 535                 540

Ser Gln Phe Thr Asn Glu Pro Val Gln Leu Thr Pro Asp Asp Asp Asp
545                 550                 555                 560

Ile Val Arg Lys Ile Asp Gln Ser Glu Phe Glu Gly Phe Glu Tyr Ile
                565                 570                 575

Asn Pro Leu Leu Met Ser Ala Glu Glu Cys Val
            580                 585

( 2 ) INFORMATION FOR SEQ ID NO:3:

( i ) SEQUENCE CHARACTERISTICS:

```
        ( A ) LENGTH: 27 base pairs
        ( B ) TYPE: nucleic acid
        ( C ) STRANDEDNESS: Not Relevant
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( x i ) SEQUENCE DESCRIPTION: SEQ ID NO:3:

GCTGACGAAT  TCGGSATGTG  YAARGAA                                                        27

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( x i ) SEQUENCE DESCRIPTION: SEQ ID NO:4:

CAGCACAAGC  TTVGMCCACC  AGTCBAC                                                        27

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( x i ) SEQUENCE DESCRIPTION: SEQ ID NO:5:

GGATGAAGCT  TTGCCACTTT  CCCTGGTGTT  CATTGC                                             36
```